United States Patent
Shah et al.

(10) Patent No.: US 10,500,309 B2
(45) Date of Patent: Dec. 10, 2019

(54) ABSORBABLE ADHESIVES AND THEIR FORMULATION FOR USE IN MEDICAL APPLICATIONS

(75) Inventors: Bhavin Shah, West Lafayette, IN (US); Paul J. Hall, Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 909 days.

(21) Appl. No.: 12/236,751

(22) Filed: Sep. 24, 2008

(65) Prior Publication Data

US 2009/0092651 A1    Apr. 9, 2009

Related U.S. Application Data

(60) Provisional application No. 60/977,680, filed on Oct. 5, 2007.

(51) Int. Cl.
| A61L 15/44 | (2006.01) |
| A61K 9/70 | (2006.01) |
| A61L 27/36 | (2006.01) |
| A61L 24/10 | (2006.01) |
| A61L 27/34 | (2006.01) |

(52) U.S. Cl.
CPC ......... *A61L 27/3633* (2013.01); *A61L 24/104* (2013.01); *A61L 27/34* (2013.01); *A61L 27/3629* (2013.01)

(58) Field of Classification Search
CPC .................................................. A61L 24/104
See application file for complete search history.

(56) References Cited

U.S. PATENT DOCUMENTS

| | | | |
|---|---|---|---|
| 3,029,188 A | 4/1962 | Gilman et al. | |
| 3,851,574 A * | 12/1974 | Katz ..................... | A23L 1/1812 206/221 |
| 4,356,819 A | 11/1982 | Potaczek | |
| 4,359,047 A | 11/1982 | Potaczek | |
| 4,361,552 A | 11/1982 | Baur, Jr. | |
| 4,695,465 A | 9/1987 | Kigasawa et al. | |
| 4,889,844 A | 12/1989 | Silvetti, Sr. et al. | |
| 4,902,508 A | 2/1990 | Badylak et al. | |
| 4,956,178 A | 9/1990 | Badylak et al. | |
| 5,177,065 A * | 1/1993 | Silvetti et al. ................... | 514/53 |
| 5,201,745 A | 4/1993 | Tayot et al. | |
| 5,209,776 A | 5/1993 | Bass et al. | |
| 5,281,422 A | 1/1994 | Badylak et al. | |
| 5,292,362 A | 3/1994 | Bass et al. | |
| 5,554,389 A | 9/1996 | Badylak et al. | |
| 5,993,844 A | 11/1999 | Abraham et al. | |
| 6,099,567 A | 8/2000 | Badylak et al. | |
| 6,190,689 B1 * | 2/2001 | Hoffmann .............. | A01N 25/24 424/447 |
| 6,206,931 B1 | 3/2001 | Cook et al. | |
| 6,325,810 B1 * | 12/2001 | Hamilton et al. ............. | 606/151 |
| 6,375,989 B1 | 4/2002 | Badylak et al. | |
| 6,379,710 B1 | 4/2002 | Badylak et al. | |
| 6,576,618 B1 | 6/2003 | Herndon et al. | |
| 7,060,708 B2 * | 6/2006 | Piccariello et al. .......... | 514/282 |
| 9,265,858 B2 * | 2/2016 | Larsen ...................... | A61L 2/04 |
| 2004/0093029 A1 | 5/2004 | Zubik et al. | |
| 2004/0105834 A1 * | 6/2004 | Singh ................... | A61C 19/066 424/70.13 |
| 2006/0004407 A1 | 1/2006 | Hiles et al. | |
| 2006/0173470 A1 | 8/2006 | Oray et al. | |
| 2007/0202173 A1 * | 8/2007 | Cueto-Garcia ............... | 424/484 |
| 2012/0288533 A1 * | 11/2012 | Livney .......................... | 424/400 |

FOREIGN PATENT DOCUMENTS

| EP | 1520525 | 4/2005 |
| WO | WO 03/002165 | 1/2003 |

OTHER PUBLICATIONS

Schuler, Thesis, Evaluation of novel cross-linking agents for gelatin/collagen matrices, 2004, Abstract.*
Sung et al., Gelatin-derived bioadhesives for closing skin wounds: an in vivo study, J. Biomaterials Sci., Polym. Ed., 1999, vol. 10, pp. 751-771.*
Dimitrove, Therapeutic proteins, Methods Mol. Biol., 2012, Abstract.*
Yoo et al. (Measurement of dynamic rheology during ageing of gelatin-sugar composites, Int. J. of Food Sci. and Tech., 2004, vol. 39, pp. 935-945).*
Heeschen C. et al., Nature Medicine 7 (2001), No. 7, 833-839.
Johnson C. et al., Circulation Research 94 (2004), No. 2, 262-268.

* cited by examiner

*Primary Examiner* — Kyle A Purdy
(74) *Attorney, Agent, or Firm* — Woodard, Emhardt, Henry, Reeves & Wagner, LLP

(57) ABSTRACT

Described are medical products including an adhesive containing a polypeptide component such as gelatin and a tackiness-providing polyhydroxy compound, such as at least one compound selected from the group consisting of glycerin and fructose. Such medical products can find use as a bolster material for use in conjunction with a surgical fastening device such as a stapler. Other medical applications utilizing a medical product of the invention include tissue repair and pharmaceutical delivery to a desired location. Related methods of manufacture and use are also described.

24 Claims, 4 Drawing Sheets

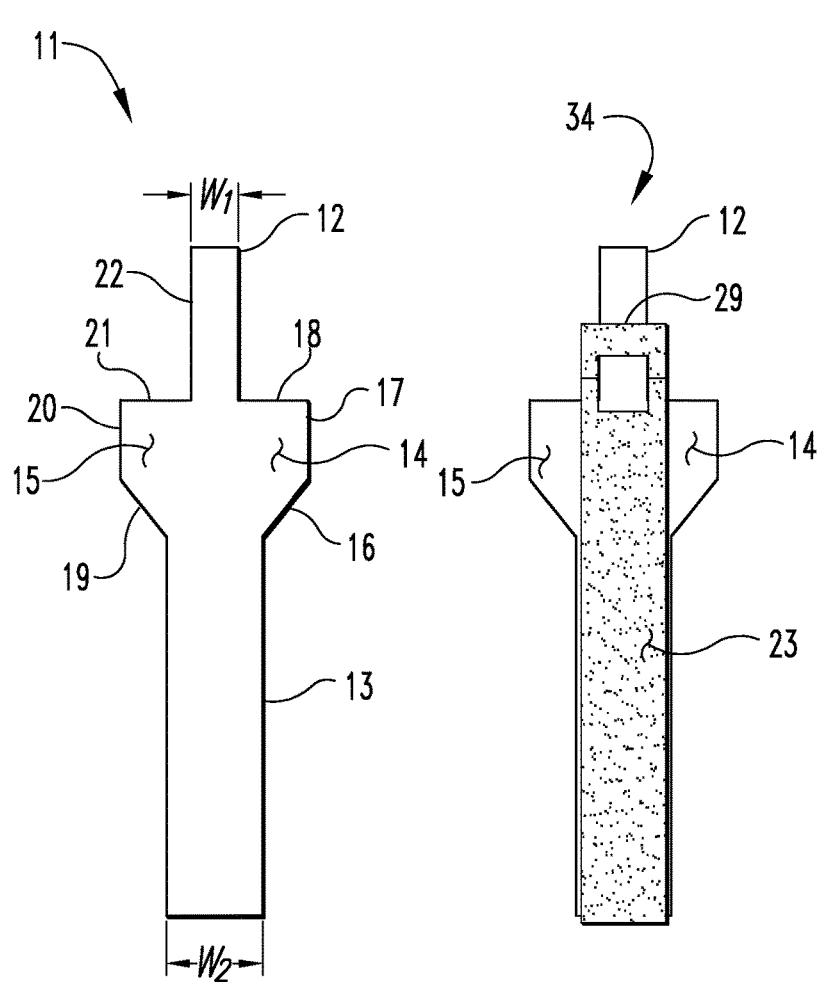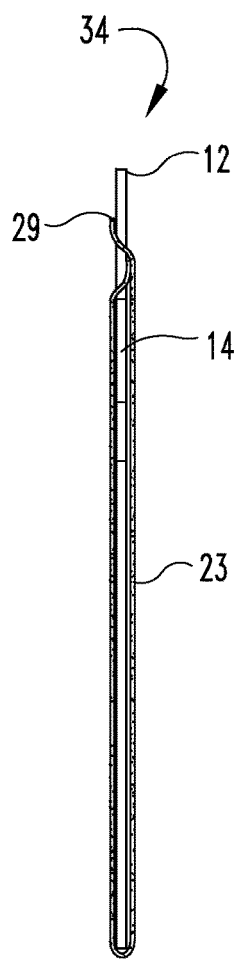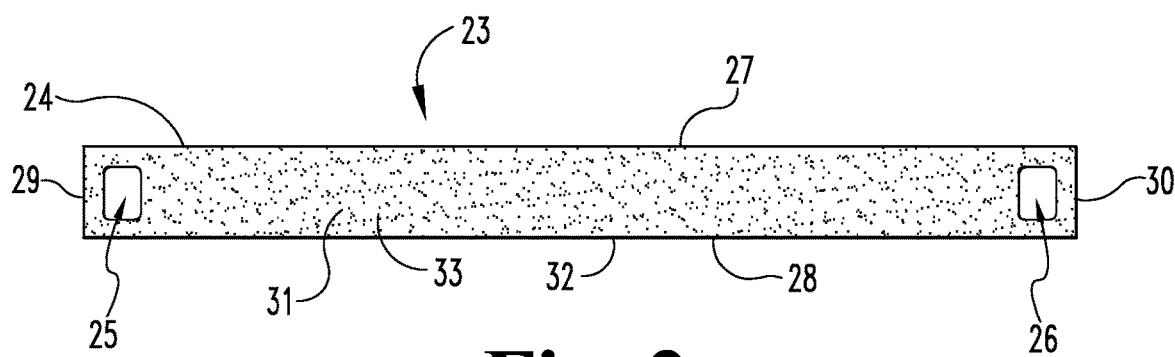
Fig. 1    Fig. 3    Fig. 4
Fig. 2

ABSORBABLE ADHESIVES AND THEIR FORMULATION FOR USE IN MEDICAL APPLICATIONS

REFERENCE TO RELATED APPLICATION

The present application claims the benefit of U.S. Provisional Patent Application Ser. No. 60/977,680 filed Oct. 5, 2007 entitled "Absorbable Adhesives and Their Formulation for Use in Medical Applications" which is hereby incorporated by reference in its entirety.

BACKGROUND

The present invention resides generally in the field of medical adhesives and in particular aspects to materials and devices including such adhesives for use in a variety of medical applications.

As further background, medical adhesives have been utilized in medical applications either alone or in conjunction with medical materials. When included on a medical material, the material can be applied to a patient as a tissue graft, or can be further included as part of a medical device, e.g., a surgical stapler.

Medical adhesives have been used on both synthetic and biological materials. With respect to biological materials, a variety of extracellular matrix (ECM) materials have been proposed for use in medical grafting, cell culture, and other related applications. For instance, medical grafts and cell culture materials containing submucosa derived from small intestine, stomach or urinary bladder tissues, have been proposed. See, e.g., U.S. Pat. Nos. 4,902,508, 4,956,178, 5,281,422, 5,554,389, 6,099,567 and 6,206,931. In addition, Cook Biotech Incorporated, West Lafayette, Ind., currently manufactures a variety of medical products based upon small intestinal submucosa under the trademarks SURGISIS®, STRATASIS® and OASIS®.

Medical materials derived from liver basement membrane have also been proposed, for example in U.S. Pat. No. 6,379,710. As well, ECM materials derived from amnion (see e.g. U.S. Pat. Nos. 4,361,552 and 6,576,618) and from renal capsule membrane (see International PCT Patent Application No. WO 03/002165 published Jan. 9, 2003) have been proposed for medical and/or cell culture applications. Any adhesive included on a medical material must be compatible with both the material and any tissue it is applied to. Adhesives having the ability to serve as a carrier for pharmaceutical or other bioactive agents are also desirable.

In certain applications, medical materials have been used in conjunction with surgical stapler devices as a bolster material. Such devices are designed to seal or simultaneously cut and seal an extended segment of tissue in a patient with staples, and a bolster material can be used to further secure the staples. The use of a bolster material finds particular use when the patient's tissue to be sealed is too fragile to securely hold the staples in place. For example, in the case of lung tissue, and in particular diseased lung tissue, the tissue to be stapled is fragile and, in extreme cases, will easily tear through unprotected staple lines. With the growing use of surgical staplers in operations on diseased lung tissues such as bullectomies and volume reduction procedures, it has become increasingly important to take measures to protect fragile tissue from tissue tears due to surgical staples or surgical stapling procedures. In many cases, as a preliminary step, the bolster material is in some manner applied to the arms of the surgical stapler, e.g. with portions applied to each arm, and the stapler thereafter used to secure tissue of the patient. In such applications, it is desirable to apply the bolster material in a manner that it is easily removable from the arms of the surgical stapler, such as after the staples have been forced through the material. Adhesives have been used for this purpose.

With respect to the above, it is apparent that a need remains for improved medical adhesives that can be used in a wide variety of medical applications. The present invention provides such medical adhesives, as well as medical products and methods related thereto.

SUMMARY

In one aspect, the present invention provides a medical product including a medical material and a dried, reversible adhesive coating formed with a mixture of two or more macromolecular substances, with the adhesive mixture coated on at least a portion of a surface of the medical material. In advantageous embodiments, the adhesive coating includes a polypeptide component, such as gelatin, that exhibits a capacity for thermally-reversible crosslinking, and at least one polyhydroxy compound, such one or both of glycerin and fructose. The medical material can be a graft material comprised of either a synthetic or a biological material. In preferred embodiments, the medical material is comprised of a biological material, such as a collagenous extracellular matrix (ECM) material.

In another aspect, the present invention provides a medical product including a layer of dried, collagenous extracellular matrix (ECM) material and a dried adhesive coating on at least a portion of a surface of the layer. The adhesive coating includes a polypeptide component, for example gelatin, and a polyhydroxy compound, such as at least one compound selected from the group consisting of glycerin and fructose. In certain preferred embodiments, the layer of dried, collagenous extracellular matrix material comprises submucosa of a warm-blooded vertebrate.

In another aspect, the present invention provides a method for preparing a medical product. The method includes providing a medical material as a first layer and applying an adhesive to at least a portion of a surface of the first layer to form an adhesive coating on the material. The adhesive includes a polypeptide component such as gelatin and a polyhydroxy compound, such as at least one compound selected from the group consisting of glycerin and fructose. The medical material including an adhesive coating is dried so as to form the medical product. Medical products of the invention find use in a wide variety of medical applications. For example, a medical product of the invention can find use as a bolster material for application to a working surface of a surgical fastening device; as a tissue repair graft, such as a hernia repair graft; and/or as a carrier for a bioactive component and/or a pharmaceutical agent.

Additional embodiments as well as features and advantages of the invention will be apparent from the further descriptions herein.

BRIEF DESCRIPTION OF THE DRAWINGS

FIG. 1 provides a front view of an applicator element that can be used in a medical combination product of the invention.

FIG. 2 provides a front view of a medical product of the invention formed as a bolster material and including a dried adhesive coating.

FIG. 3 provides a front view of a medical device including the applicator element and material product of FIGS. 1 and 2, respectively.

FIG. 4 provides a right end view of the medical device of FIG. 3.

DETAILED DESCRIPTION

Figure 5:
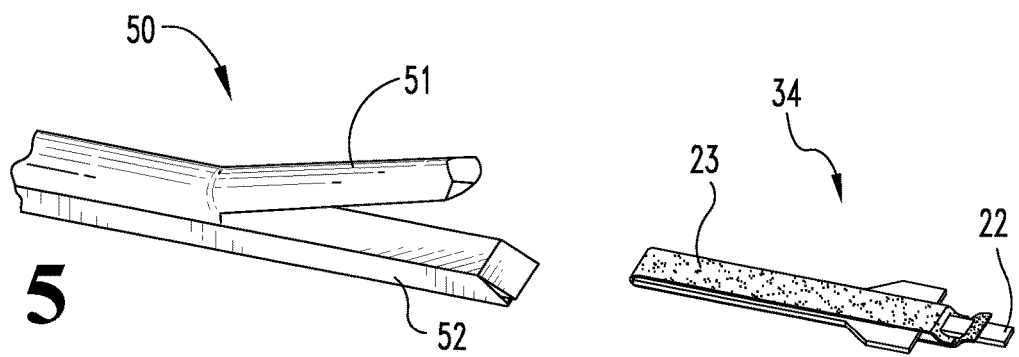
FIGS. 5-9 depict steps for applying the bolster material of FIG. 2 to a surgical stapler using the applicator element of FIG. 1.

For the purposes of promoting an understanding of the principles of the invention, reference will now be made to the embodiments illustrated in the drawings and specific language will be used to describe the same. It will nevertheless be understood that no limitation of the scope of the invention is thereby intended, and alterations and modifications in the illustrated materials and devices, and further applications of the principles of the invention as illustrated therein are herein contemplated as would normally occur to one skilled in the art to which the invention relates.

As disclosed above, in certain aspects, the present invention provides medical products useful in a wide variety of medical applications. Such medical products include a dried, reversible adhesive containing a polypeptide component, desirably gelatin, and a polyhydroxy compound, preferably at least one compound selected from the group consisting of glycerin and fructose. In particularly preferred embodiments, adhesives exhibit a glass transition temperature in the range of about 37° C. Desirable adhesives can also have a low melting point and slow solubility in water. In addition, both water soluble and water insoluble agents can be included in the adhesive.

In preferred embodiments, medical products of the invention are bolster materials that can be used in conjunction with a surgical fastening device, such as a surgical stapler. In such embodiments, it will be understood that a medical product of the invention may be used in conjunction with a variety of surgical fastening devices that insert fasteners of various designs, including for example one-part and multiple (e.g. two) part staples, tacks, or other penetrating fasteners where bolstering may provide a benefit. Suitable surgical fastening devices include those described in, for instance, U.S. patent application Ser. No. 11/060,078, published Jan. 5, 2006 as United States Patent Application Publication No. 20060004407.

With reference now to FIGS. 1-4, shown is a medical device including a medical product of the invention. FIG. 1 shows a plan view of an applicator element 11 useful in the present invention. Applicator element 11 includes a body 12 to be used in conjunction with a medical product formed as a staple bolster material. Body 12 is desirably formed all or in part of a compressible material, for example a polymer foam. Body 12 may, for example, be made from Styrofoam or another similar material. Body 12 may be both compressible and resilient, such that it returns substantially to its original shape after compress, or may be compressible and relatively non-resilient, such that it is crushable upon compression so as to permanently adopt its crushed condition. It will be understood, however, that body 12 can be made of other suitable materials as well.

The illustrated body 12 generally includes a first rectangular portion 13 for accommodating a strip of staple bolster material, the rectangular portion 13 terminating in a generally wider portion including a first laterally extending portion 14 and a second laterally extending portion 15. Laterally extending portions 14 and 15 can, for instance, provide a segment of material that will extend laterally from the arms of a surgical stapler closed around applicator element 11. In this fashion, a user may grip portions 14 and 15 before and during the loading procedure. Lateral portion 14 is defined by first edge portion 16 extending transversely from the outside edge of generally rectangular portion 13. Edge 16 may form an angle greater than, less than, or equal to 90° relative to the outer edge of rectangular portion 13. Desirably, as illustrated, edge 16 forms a generally obtuse angle relative to the outer edge of rectangular portion 13. Lateral portion 14 is bounded by outer edge 17 which, as shown, is generally parallel the outer edge of the rectangular portion 13, although any other suitable relationship is contemplated. Lateral element 14 as illustrated also includes a third edge 18 which as shown is generally perpendicular to the outer edge of rectangular portion 13. The illustrated applicator element 11 includes a corresponding and opposed lateral element 15 defined by edge 19, 20, and 21 that are similar to edges 16, 17, and 18, respectively. It will be understood that in embodiments of the present invention including lateral extensions, the configuration of the lateral extension may take any form suitable to provide a segment to provide a user grip. For example, lateral extensions may be formed as generally triangular sections, rectangular sections, or circular segments, e.g. semi-circular portions, extending laterally of the rectangular portion 13. Applicator element 11 also includes an engaging end 22 for engaging a staple bolster material. Engaging end 22 desirably forms a shoulder at an intersection with a wider portion of applicator element 11, for example including a width W1 generally less than that of the adjacent portion including lateral extensions 14 and 15, optionally with width W1 being less than or about equal to width W2 of the rectangular portion 13, although this is not necessary to the broader aspects of the present invention.

With reference now to FIG. 2, shown is a medical product of the invention formed into an inventive strip of staple bolster material 23 that can be used in conjunction with applicator element 11 of FIG. 1. Staple bolster strip 23 includes a generally elongate body 24 having a first opening 25 and a second opening 26. Openings 25 and 26 can be of any suitable size and dimension, including slits, apertures, or other openings suitable for use in conjunction with cooperating engaging portions of applicator elements. Staple bolster strip 23 as shown is generally rectangular in its external shape including first elongate edge 27, second elongate edge 28, and end edges 29 and 30 extending generally perpendicular thereto. Such a configuration results in a material having a first surface 31 and a second surface 32 opposing first surface 31. As shown, first surface 31 includes a dried, reversible adhesive coating 33 including gelatin and a compound selected from the group consisting of glycerin and fructose. The coating can be applied to at least a portion of a surface of staple bolster strip 23. Typically, the coating is applied to a substantial portion of the surface of the strip opposing the surface that contacts applicator element 11. Staple bolster strip 23 can be made from any suitable material to bolster a staple line or single staple, including those materials described hereinbelow.

With reference now to FIG. 3, shown is an assembled medical device 34 useful for applying a staple bolster material to a surgical stapler, having staple bolster strip 23 coupled to applicator element 11. In particular, in one mode of assembly, engaging portion 22 of applicator element 11 can be inserted through aperture 26 adjacent to end 30 of the staple bolster strip 23. Staple bolster strip 23 can then be extended down and around generally rectangular portion 13 so as to encompass both sides thereof. Applicator element 11 can then be deformed as necessary to insert the engaging portion 22 through aperture 25 adjacent end 29. This will provide an arrangement as illustrated, in which the staple bolster strip 23 is wrapped around element 11 and secured thereto with the help of engaging portion 22 which extends through apertures 25 and 26 of staple bolster strip 23. With reference to FIG. 4, shown is a right-end view of the medical device 34 of FIG. 3. As shown, staple bolster strip 23 is wrapped around applicator element 11, with the engaging portion 22 extending through apertures 25 and 26.

Figure 6:
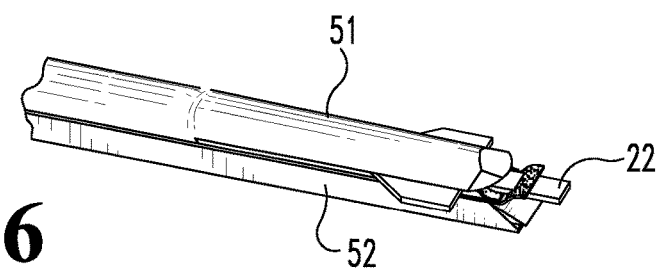
Figure 7:
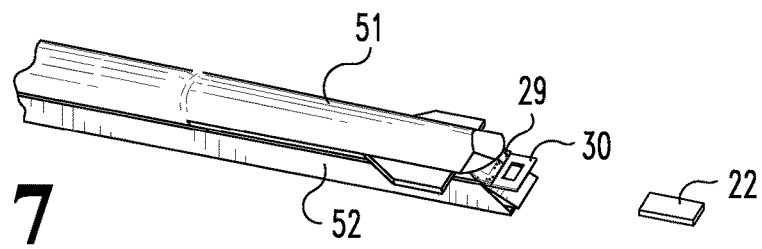
Figure 8:
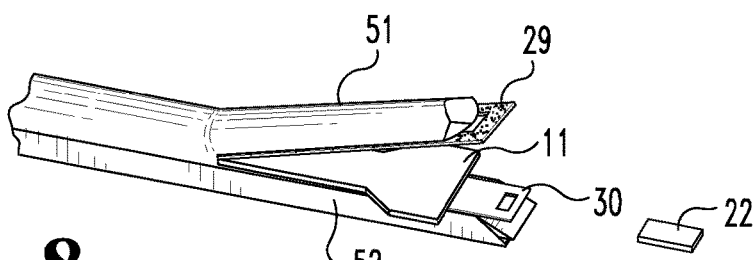
Figure 9:
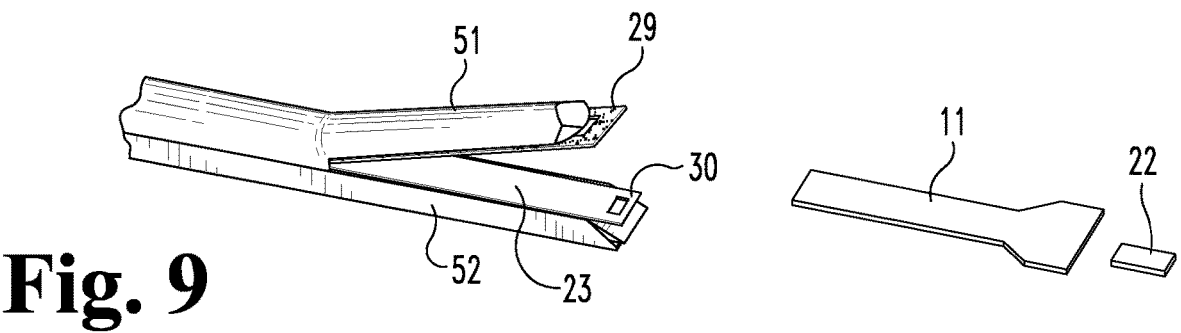

With reference now to FIGS. 1-4 together with FIGS. 5-9, an illustrative manner of using the medical device 34 in conjunction with a surgical stapler 50 will be described. With the arms 51 and 52 of the surgical stapler in an open condition (see FIG. 5), the assembled medical device 34 can be inserted between the arms of the surgical stapler 50 so as to align the staple bolster strip 23 with the opposed surfaces of the respective arms. The arms are closed around the medical device 34 so as to bring the opposed surfaces in contact with the staple bolster strip 23 on opposite sides thereof, as shown in FIG. 6. Staple bolster strip 23 is caused to adhere to the stapler arm surfaces by virtue of adhesive coating 33. For these purposes, the adhesive, the stapler arm, or both, can be wetted in order to render the adhesive material tacky. Any suitable wetting agent can be used. Aqueous mediums can be used, including for example saline solution or high purity water. With the arms in the closed condition, the engaging portion 22 can be separated from the remainder of the applicator element 11 so as to cause a release of the ends 29 and 30 of the staple bolster strip 23, as shown in FIG. 7. As examples, the separation of the engaging portion 22 can be caused by tearing or cutting. After the separation of the engaging portion and release of the staple bolster ends 29 and 30, the arms 51 and 52 are caused to separate, whereupon staple bolster strip 23 remains adhered to and is carried apart by the arm surfaces generally forming a "V" configuration conforming to that provided by the arm surfaces. In this state, the major portion of the applicator element will remain between the arms 51 and 52 along with the staple bolster strip 23, as illustrated in FIG. 8. Applicator element 11 can then be removed from the surgical stapling device, leaving staple bolster strip 23 associated with the staple bolster device for use in reinforcing one or more staples to be implanted using the surgical stapling device 50. With reference generally to the above discussion, in another mode of use, the engaging portion 22 can be deformed or otherwise manipulated so as to be removed from the apertures 25 and 26 to disengage the ends 29 and 30 from the applicator element 11. Otherwise, the application procedure can be the same.

Figure 10:
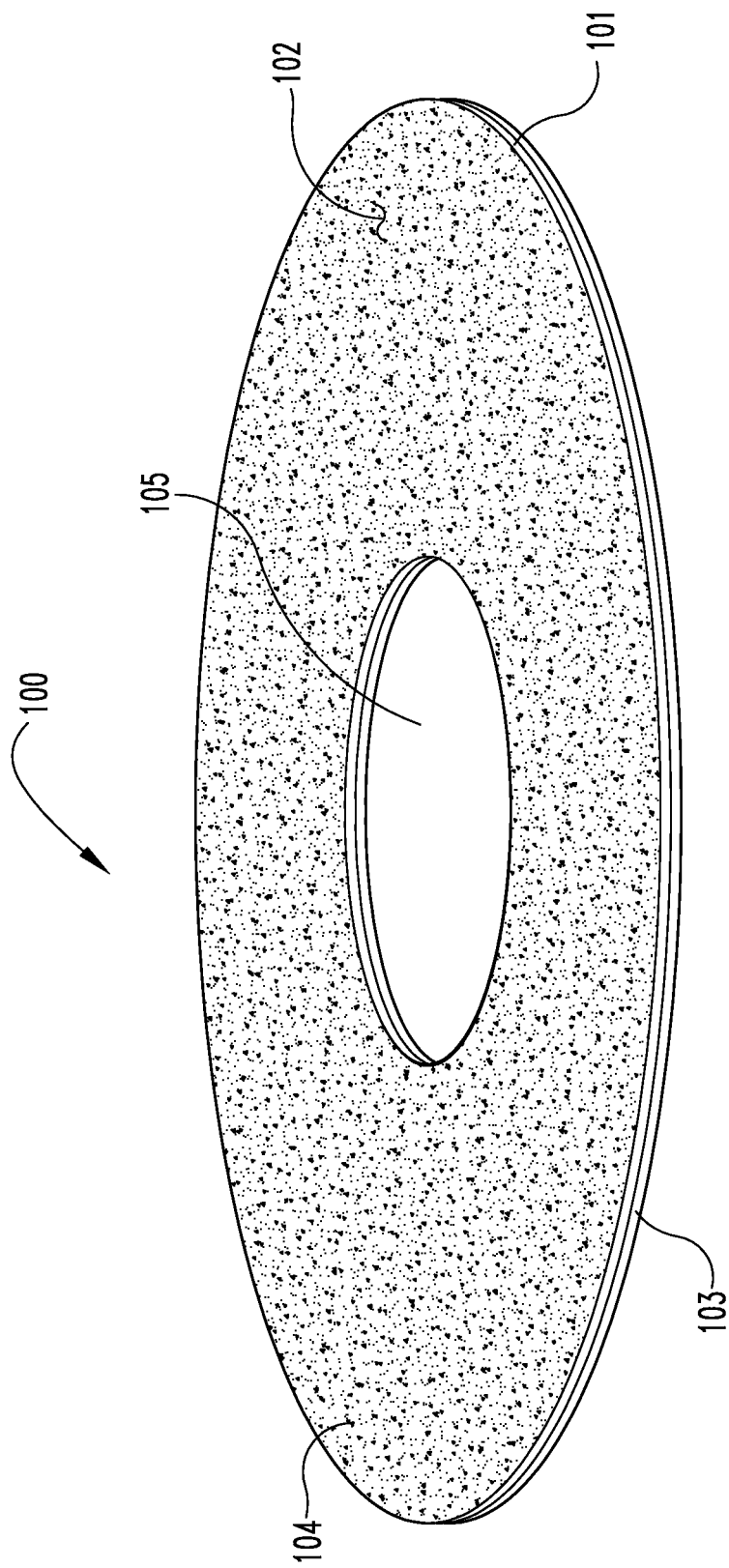
FIG. 10 provides a front view of an alternate medical product of the invention as a bolster material and including a dried adhesive coating.
Figure 11:
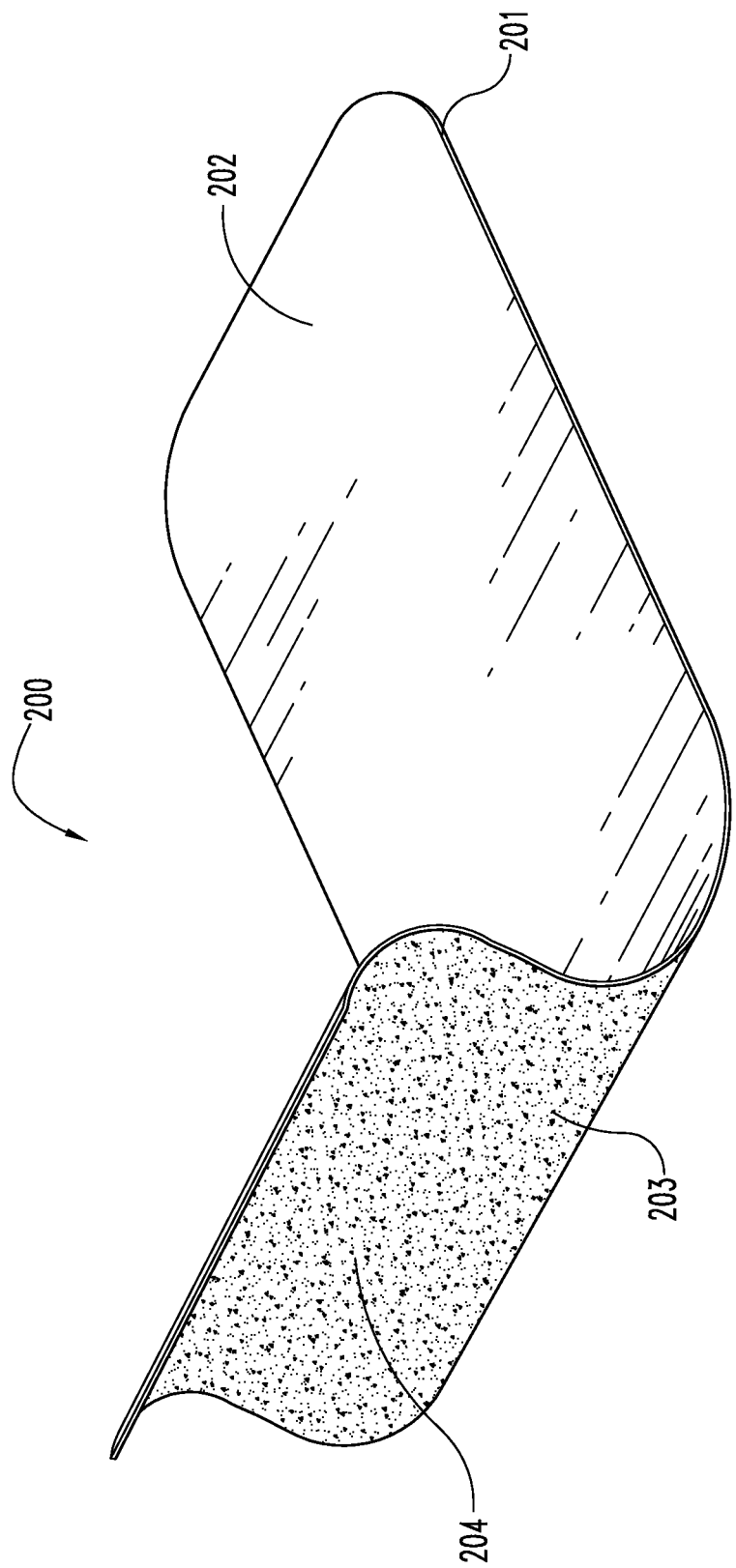
FIG. 11 provides a perspective view of a medical product of the invention useful, for example, as a hernia repair patch and including a layer of a medical material coated on a surface with a dried adhesive.

Turning now to FIG. 10, shown is another medical product 100 for use in staple bolster applications. Medical product 100 includes a generally circular sheet of staple bolster material 101 coupled to an applicator 103, e.g. by releasable bonding, clips, etc. Staple bolster material 101 includes a surface 102 including an adhesive coating 104 of the present application. Adhesive coating 104 is useful, for example, to secure the sheet of circular staple bolster material 101 to a staple bolster device. To accomplish this, medical product 101 can be delivered to a staple bolster device configured for acceptance of a circular staple bolster material with opening 205 passing over an elongated central arm of the stapler and/or over any other centrally-located elements of the cartridge or anvil components. As before, staple bolster material 101 is caused to adhere to a stapler working surface by virtue of adhesive coating 104. Again, a wetting agent as described herein can be applied to the adhesive, the working surface, or both, for these purposes. Once the staple bolster material 101 has been delivered to a stapler working surface, the applicator 103 can be removed. If desired, a second medical product 100 can be similarly used to apply a bolster material to a second working surface of the stapler.

It will be understood that in embodiments involving a medical product being used in conjunction with a surgical fastening device, one piece, or more than one piece of staple bolster material, can be coupled to an applicator element, and bolster material may be presented at one or both sides of the applicator element. For example, separate pieces of staple bolster material can be presented on the separate sides of the applicator element as in some of the illustrated embodiments. Each piece of bolster material can be held in association with the applicator element using any of the disclosed features, for example being bonded to or retained by the applicator element by having a least a portion thereof received around, through, over, etc., the applicator element. All such embodiments are contemplated as a part of the present invention. Advantageously, although not necessary to the broader aspects of the invention, in certain embodiments, the bolster material will be retained in association with the applicator element without the use of any other mechanical component (e.g. a clip) compressing or otherwise holding the bolster material in contact with the applicator element. Thus, a bolster applicator device consisting of, or consisting essentially of, the applicator element and bolster material may be presented between the arms of the surgical stapler for the bolster loading operation. In alternative embodiments, a clip, sheath or other similar element can be used to maintain the bolster material in contact with the applicator element, including for example embodiments as disclosed in U.S. patent application Ser. No. 10/414,432, published May 13, 2004 as United States Patent Application Publication No. 20040093029, and in U.S. patent application Ser. No. 11/047,477, published Aug. 3, 2006 as United States Patent Application Publication No. 20060173470.

When a medical product is used as a staple bolster material in the context of the invention, it may be desirable to bond areas of the medical product to one another, for example in securing the medical product around all or a portion of an associated applicator element. A medical adhesive may be used for this purpose and can be the adhesive discussed herein. In addition or alternatively, medical product layers (e.g., collagenous layers), can be dehydrothermally bonded to one another, for example by drying the layers in contact with one another, e.g. under compression. The drying operation can, for example, occur in a lyophilization (freeze drying) or vacuum pressing process.

In additional embodiments, a medical product can be used in a variety of medical applications other than staple bolstering. For example, FIG. 10 depicts a medical product 200 of the invention useful, for example, in tissue repair. Medical product 200 includes a layer of a medical material 201 including a first surface 202 and a second surface 203 opposing first surface 202. Second surface 203 includes a dried, reversible adhesive coating 204 containing gelatin and a compound selected from the group consisting of glycerin and fructose. Although not pictured, medical product 200 can optionally include a release paper covering adhesive coating 204. Such a release paper finds use, for instance, to protect the adhesive coating 204 prior to its application to tissue or device. In particular, a release paper can be included where a medical product is contained within a sterile package prior to use. A release paper can be made of any suitable material and is preferably made of a non-stick material, such as Tyvek®. This material can stick to the adhesive coating, but is generally non-adhesive towards other surfaces. In this respect, a non-adhesive release paper will not stick to the walls of a sterile package when the medical product is stored for any period of time. Just prior to use, the release paper can be removed, and the medical product can be applied to a desired tissue or device.

Medical products of the invention, such as medical products 23, 100 and 200 can be used to treat a variety of tissue defects including the repair or reconstruction of nervous tissue, skin, cardiovascular tissue (including vascular tissue and cardiac tissue), pericardial tissue, muscle tissue, ocular tissue, periodontal tissue, bone, connective tissue such as tendons or ligaments, and others. Preferably, a medical product of the invention can be used to treat structural tissue defects, including those involving uroepithelium (e.g., bladder, urethra, ureter), gastrointestinal mucosa (e.g., oropharynx, esophagus, stomach, intestine), respiratory epithelium (e.g., trachea, bronchus) and vasculature (e.g., artery, vein, lymphatics). Medical products of the invention can be used in hernia repair, such as epigastric, umbilical, incisional, hiatal, femoral, and inguinal hernia repair. A hernia is described as the protrusion of an organ through a tissue, which may occur anywhere in the body. When in the lower abdominal area, it often involves penetration of the intestine into or through the abdominal wall. The medical product of the invention can be applied to the site of a hernia, and can be used in conjunction with surgery, if deemed necessary, to treat a patient having a hernia.

Generally, when configured for tissue repair, the medical product of the invention is cut or otherwise configured to a desired size for its end use. The medical product is preferably sized larger than the tissue defect to which it is applied. Sizing the medical material in this way allows for easy attachment to the surrounding tissue.

Although the adhesive coating can be sufficient to secure the medical product in place, it may, in certain instances, be advantageous to more securely attach the medical product to tissue. For example, once the medical product has been placed on, in, or around the defect, the medical product can be more securely attached to the surrounding tissue using any of several known suitable attachment means. Suitable attachment means include, for example, stapling, suturing, and the like. In many embodiments, the medical material will be more securely attached to the surrounding tissue by sutures. There are a variety of synthetic materials currently available in the art for use as sutures. For example, sutures comprising Prolene™, Vicryl™, Mersilene™, Panacryl™, and Monocryl™, are contemplated for use in the invention. Other suture materials will be well known to those skilled in the art. The aforementioned materials therefore serve merely as examples and, consequently, are in no way limiting.

The medical product of the invention can be in a dehydrated or hydrated state. Dehydration of a medical product of the invention can be achieved by any means known in the art. Preferably, dehydration is accomplished by lyophilization, drying in a vacuum, air drying, heated (e.g. oven) drying, or any combination of these. Typically, the medical product will be dehydrated when it is to be stored for a period of time. Any suitable solution can then be used to rehydrate the medical material prior to use. Preferably, the rehydration solution comprises water or buffered saline. In certain embodiments, hydrating the medical product will activate the adhesive such that it can adhere to tissue or a device. The above-described methods of dehydration and rehydration of the medical product allow for an effective shelf life and convenient packaging.

In certain embodiments, the medical product can be crosslinked. A medical product can be crosslinked once formed, or the of medical material and adhesive can be crosslinked separately before the adhesive is applied to the material, or both. Increasing the amount (or number) of crosslinkages within the medical product or between two or more layers of the medical material can be used to enhance its strength. However, when a remodelable material is used, the introduction of crosslinkages within the material may also affect its resorbability or remodelability. Consequently, in certain embodiments, a remodelable ECM material used in a medical product will substantially retain its native level of crosslinking, or the amount of added crosslinkages within the medical material will be judiciously selected depending upon the desired treatment regime. In many cases, the medical material will exhibit remodelable properties such that the remodeling process occurs over the course of several days or several weeks. In certain preferred embodiments, the remodeling process occurs within a matter of about 5 days to about 12 weeks.

For use in the present invention, introduced crosslinking of the medical product may be achieved by photo-crosslinking techniques, or by the application of a crosslinking agent, such as by chemical crosslinkers, or by protein crosslinking induced by dehydration or other means. Chemical crosslinkers that may be used include for example aldehydes such as glutaraldehydes, diimides such as carbodiimides, e.g., 1-ethyl-3-(3-dimethylaminopropyl)carbodiimide hydrochloride, ribose or other sugars, acyl-azide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

When multiple layers of a medical material are used to form a laminate material, the layers of the laminate can be additionally crosslinked to bond multiple layers of medical material to one another. Thus, additional crosslinking may be added to individual layers prior to coupling to one another, during coupling to one another, and/or after coupling to one another.

Any suitable medical material can be used in the context of the present invention. The medical material is generally biocompatible and can be a synthetic or a biological material. In preferred embodiments, the medical material is a biological material. Other implantable materials that may be employed as medical materials in the present invention include non-bioresorbable or bioresorbable synthetic polymer materials such as polytetrofluoroethylene (PTFE, e.g. GORE-TEX material), nylon, polypropylene, polyurethane, silicone, DACRON polymer, polyglycolic acid (PGA), polylactic acid (PLA), polycaprolactone, or others.

It is advantageous to use a remodelable material in the medical products and methods of the present invention, and particular advantage can be provided by including a remodelable collagenous material. Such remodelable collagenous materials can be provided, for example, by collagenous materials isolated from a suitable tissue source from a warm-blooded vertebrate, and especially a mammal. Reconstituted or naturally-derived collagenous materials can be used in the present invention. Such materials that are at least bioresorbable will provide advantage in the present invention, with materials that are bioremodelable and promote cellular invasion and ingrowth providing particular advantage. Remodelable materials may be used in this context to promote cellular growth within the site in which a medical product of the invention is implanted. Moreover, the thickness of the medical product can be adjusted to control the extent of cellular ingrowth.

Suitable bioremodelable materials can be provided by collagenous extracellular matrix materials (ECMs) possessing biotropic properties, including in certain forms angiogenic collagenous extracellular matrix materials. For example, ECMs include materials such as submucosa, renal capsule membrane, dermal collagen, dura mater, pericardium, fascia lata, serosa, peritoneum or basement membrane layers, including liver basement membrane. Suitable submucosa-containing materials for these purposes include, for instance, materials that include intestinal submucosa, including small intestinal submucosa, stomach submucosa, urinary bladder submucosa, and uterine submucosa. These identified submucosa or other layers can occur in the ECM material alone, or in combination with other materials such as those derived from one or more adjacent layers in the source tissue.

The submucosa-containing ECM can be derived from any suitable organ or other biological structure, including for example submucosa derived from the alimentary, respiratory, intestinal, urinary or genital tracts of warm-blooded vertebrates. Submucosa-containing materials useful in the present invention can be obtained by harvesting such tissue sources and delaminating the submucosa (alone or combined with other materials) from smooth muscle layers, mucosal layers, and/or other layers occurring in the tissue source. For additional information as to submucosal materials useful in the present invention, and its isolation and treatment, reference can be made, for example, to U.S. Pat. Nos. 4,902,508, 5,554,389, 5,993,844, 6,206,931, and 6,099,567.

When a submucosal or other ECM material having differing characteristic sides is used in combination with a medical device, e.g., a surgical stapler, it can be oriented upon the medical device with a specified side directed outward for contact with the arm(s) of the surgical fastening device. For example, in the case of small intestinal submucosa, the material may be oriented with either the luminal or abluminal side facing the working surface(s) of the surgical fastening device.

As prepared, the submucosal material and any other ECM used may optionally retain growth factors or other bioactive components native to the source tissue. For example, the submucosal or other ECM may include one or more native growth factors such as basic fibroblast growth factor (FGF-2), transforming growth factor beta (TGF-beta), epidermal growth factor (EGF), and/or platelet derived growth factor (PDGF). As well, submucosa or other ECM used in the invention may include other biological materials such as heparin, heparin sulfate, hyaluronic acid, fibronectin and the like. Thus, generally speaking, the submucosa or other ECM material may include a native bioactive component that induces, directly or indirectly, a cellular response such as a change in cell morphology, proliferation, growth, protein or gene expression.

Submucosal or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive components, the ECM material can retain these components interspersed as solids between, upon and/or within the collagen fibers. Particularly desirable naturally-derived ECM materials for use in the invention will include significant amounts of such interspersed, non-collagenous solids that are readily ascertainable under light microscopic examination. Such non-collagenous solids can constitute a significant percentage of the dry weight of the ECM material in certain inventive embodiments, for example at least about 1%, at least about 3%, and at least about 5% by weight in various embodiments of the invention.

The submucosal or other ECM material used in the present invention may also exhibit an angiogenic character and thus be effective to induce angiogenesis in a host engrafted with a device including the material. In this regard, angiogenesis is the process through which the body makes new blood vessels to generate increased blood supply to tissues. Thus, angiogenic materials, when contacted with host tissues, promote or encourage the formation of new blood vessels. Methods for measuring in vivo angiogenesis in response to biomaterial implantation have recently been developed. For example, one such method uses a subcutaneous implant model to determine the angiogenic character of a material. See, C. Heeschen et al., *Nature Medicine* 7 (2001), No. 7, 833-839. When combined with a fluorescence microangiography technique, this model can provide both quantitative and qualitative measures of angiogenesis into biomaterials. C. Johnson et al., *Circulation Research* 94 (2004), No. 2, 262-268.

Further, in addition or as an alternative to the inclusion of native bioactive components, non-native bioactive components such as those synthetically produced by recombinant technology or other methods, may be incorporated into the submucosal or other ECM tissue. These non-native bioactive components may be naturally-derived or recombinantly produced proteins that correspond to those natively occurring in the ECM tissue, but perhaps of a different species (e.g. human proteins applied to collagenous ECMs from other animals, such as pigs). The non-native bioactive components may also be drug substances. Illustrative drug substances that may be incorporated into and/or onto the ECM materials used in the invention include, for example, antibiotics, thrombus-promoting substances such as blood clotting factors, e.g. thrombin, fibrinogen, and the like. These substances may be applied to the ECM material as a premanufactured step, immediately prior to the procedure (e.g. by soaking the material in a solution containing a suitable antibiotic such as cefazolin), or during or after engraftment of the material in the patient. Alternatively or additionally, a non-native bioactive component can be included in the adhesive coating of the medical product. When included in the adhesive, the non-native bioactive component can be added at any point during preparation of the medical product, including being mixed with one or all of the adhesive components prior to application of the adhesive to a surface of a layer of a medical material or, alternatively, after the adhesive is formed and applied.

A non-native bioactive component can be applied to a submucosal or other ECM tissue by any suitable means. Suitable means include, for example, spraying, impregnating, dipping, etc. The non-native bioactive component can be applied to the ECM tissue either before or after the adhesive is applied to the material, or both. Similarly, if other chemical or biological components are included in the ECM tissue, the non-native bioactive component can be applied either before, in conjunction with, or after these other components.

Submucosal or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosal or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 μg/mg, more preferably less than about 2 μg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosal tissue used in the present invention.

In additional embodiments, medical products of the invention can include ECM's or other collagenous materials that have been subjected to processes that expand the materials. In certain forms, such expanded materials can be formed by the controlled contact of an ECM material with one or more alkaline substances until the material expands, and the isolation of the expanded material. Illustratively, the contacting can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner in the preparation of a medical device. Illustratively, the expanded material can be enriched with bioactive components, dried, and/or molded, etc., in the formation of a graft construct of a desired shape or configuration. In certain embodiments, a medical graft material and/or device formed with the expanded ECM material can be highly compressible (or expandable) such that the material can be compressed for delivery, such as from within the lumen of a cannulated delivery device, and thereafter expand upon deployment from the device so as to become anchored within a patient and/or cause closure of a tract within the patient.

Expanded collagenous or ECM materials can be formed by the controlled contact of a collagenous or ECM material with an aqueous solution or other medium containing sodium hydroxide. Alkaline treatment of the material can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. The magnitude of the expansion is related to several factors, including for instance the concentration or pH of the alkaline medium, exposure time, and temperature used in the treatment of the material to be expanded.

ECM materials that can be processed to make expanded materials can include any of those disclosed herein or other suitable ECM's. Typical such ECM materials will include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness.

Illustratively, the concentration of the alkaline substance for treatment of the remodelable material can be in the range of about 0.5 to about 2 M, with a concentration of about 1 M being more preferable. Additionally, the pH of the alkaline substance can in certain embodiments range from about 8 to about 14. In preferred aspects, the alkaline substance will have a pH of from about 10 to about 14, and most preferably of from about 12 to about 14.

In addition to concentration and pH, other factors such as temperature and exposure time will contribute to the extent of expansion, as discussed above. In this respect, in certain variants, the exposure of the collagenous material to the alkaline substance is performed at a temperature of about 4 to about 45° C. In preferred embodiments, the exposure is performed at a temperature of about 25 to about 40° C., with 37° C. being most preferred. Moreover, the exposure time can range from at least about one minute up to about 5 hours or more. In some embodiments, the exposure time is about 1 to about 2 hours. In a particularly preferred embodiment, the collagenous material is exposed to a 1 M solution of NaOH having a pH of 14 at a temperature of about 37° C. for about 1.5 to 2 hours. Such treatment results in collagen denaturation and a substantial expansion of the remodelable material. Denaturation of the collagen matrix of the material can be observed as a change in the collagen packing characteristics of the material, for example a substantial disruption of a tightly bound collagenous network of the starting material. A non-expanded ECM or other collagenous material can have a tightly bound collagenous network presenting a substantially uniform, continuous surface when viewed by the naked eye or under moderate magnification, e.g. 100× magnification. Conversely, an expanded collagenous material can have a surface that is quite different, in that the surface is not continuous but rather presents collagen strands or bundles in many regions that are separated by substantial gaps in material between the strands or bundles when viewed under the same magnification, e.g. about 100×. Consequently, an expanded collagenous material typically appears more porous than a corresponding non-expanded collagenous material. Moreover, in many instances, the expanded collagenous material can be demonstrated as having increased porosity, e.g. by measuring for an increased permeability to water or other fluid passage as compared to the non-treated starting material. The more foamy and porous structure of an expanded ECM or other collagenous material can allow the material to be cast or otherwise prepared into a variety of sponge or foam shapes for use in the preparation of medical materials and devices. It can further allow for the preparation of constructs that are highly compressible and which expand after compression. Such properties can be useful, for example, when the prepared medical graft material is to be compressed and loaded into a deployment device (e.g. a lumen thereof) for delivery into a patient, and thereafter deployed to expand at the implant site.

After such alkaline treatments, the material can be isolated from the alkaline medium and processed for further use. Illustratively, the collected material can be neutralized and/or rinsed with water to remove the alkalinity from the material, prior to further processing of the material to form a medical graft material of the invention.

A starting ECM material (i.e., prior to treatment with the alkaline substance) can optionally include a variety of bioactive or other non-collagenous components including, for example, growth factors, glycoproteins, glycosaminoglycans, proteoglycans, nucleic acids, and lipids. Treating the material with an alkaline substance may reduce the quantity of one, some or all of such non-collagenous components contained within the material. In certain embodiments, controlled treatment of the remodelable material with an alkaline substance will be sufficient to create a remodelable collagenous material which is substantially devoid of nucleic acids and lipids, and potentially also of growth factors, glycoproteins, glycosaminoglycans, and proteoglycans. This may be true for other processing techniques as discussed herein, such as the controlled treatment of the material with a detergent.

In certain embodiments, one or more bioactive components, exogenous or endogenous, for example, similar to those removed from an ECM material (i.e., both non-expanded and expanded materials) during processing, can be returned to the material. For example, an ECM material can include a collagenous material which has been depleted of nucleic acids and lipids, but which has been replenished with growth factors, glycoproteins, glycosaminoglycans, and/or proteoglycans. These bioactive components can be returned to the material by any suitable method. For instance, in certain forms a tissue extract, such as is discussed in U.S. Pat. No. 6,375,989, containing these components can be prepared and applied to an ECM collagenous material. In one embodiment, the ECM can be incubated in a tissue extract for a sufficient time to allow bioactive components contained therein to associate with the ECM material. The tissue extract may, for example, be obtained from non-expanded collagenous tissue of the same type used to prepare the expanded material. Other means for returning or introducing bioactive components to an ECM material include spraying, impregnating, dipping, etc. as known in the art. By way of example, an ECM material may be modified by the addition of one or more growth factors such as basic fibroblast growth factor (FGF-2), transforming growth factor beta (TGF beta), epidermal growth factor (EGF), platelet derived growth factor (PDGF), and/or cartilage derived growth factor (CDGF). As well, other biological components may be added to an ECM material, such as heparin, heparin sulfate, hyaluronic acid, fibronectin and the like. Thus, generally speaking, an ECM material may include a bioactive component that induces, directly or indirectly, a cellular response such as a change in cell morphology, proliferation, growth, protein or gene expression similar to a non-expanded collagenous material.

With respect to the above, a medical material can be provided in any suitable form prior to application of an adhesive thereto. Suitable forms include, for example, as one or more sheets or layers, as a foam, or as a sponge. The form used will typically depend on a variety of factors including, but not limited to, the end use of the medical product and the type of material used (e.g., synthetic or biological).

In embodiments of the invention where a medical material is provided in sheet form, the medical material will have a thickness in the range of about 50 to about 1000 microns, more preferably about 100 to 600 microns, and most preferably about 100 to about 350 microns. The medical material will desirably provide sufficient strength to effectively reinforce staple(s) when the product is formed into a staple bolster material, for example exhibiting a suture retention strength in the range of about 100 to about 1000 gram force, e.g. typically in the range of about 200 to about 600 gram force, each of these based upon 5-0 Prolene suture and a bite depth of 2 mm. If necessary or desired, a multilaminate medical product can be used. For example, a plurality of (i.e. two or more) layers of a biocompatible material, for example submucosa-containing or other ECM material, can be bonded together to form a multilaminate structure. Illustratively, two, three, four, five, six, seven, or eight or more layers of a biocompatible material can be bonded together to provide a multilaminate bolster material. In certain embodiments, two to six collagenous, submucosa-containing layers isolated from intestinal tissue of a warm-blooded vertebrate, particularly small intestinal tissue, are bonded together to provide the staple bolster material. Porcine-derived small intestinal tissue is preferred for this purpose. The layers of collagenous tissue can be bonded together in any suitable fashion, including dehydrothermal bonding under heated, non-heated or lyophilization conditions, using adhesives as described herein, glues or other bonding agents, crosslinking with chemical agents or radiation (including UV radiation), or any combination of these with each other or other suitable methods.

Turning now to a discussion of the dried adhesive, said adhesive can be applied to at least a portion of a surface of a medical material by any suitable means. Suitable means include, for example, brushing, spraying, dipping, etc. Alternatively, a dried adhesive film can be separately prepared, and then attached to the medical material, e.g. by partial wetting of one side and bonding of that side to the medical material, optionally followed by re-drying. Typically, a substantial portion of a surface of a medical material is coated with the adhesive. By "substantial portion" is meant that at least about 75% of a specified surface (e.g. one side or the other of a sheet in certain circumstances) of a medical material is coated with an adhesive. In embodiments involving the use of a surgical fastening device, means of attachment will be such that it increases the efficiency of attachment of the medical product to the arm surface, so long as the attachment is not so permanent as to deleteriously interfere with release of the bolster material after the surgical stapler has been fired or otherwise actuated to insert the staple or staples. The adhesive can be applied to the medical material at the point of use, or in a pre-applied configuration. In certain embodiments, a pre-applied adhesive can be covered with release paper or similar material to protect the adhesive layer during shipping and handling. The release paper can then be removed prior to use.

A dried adhesive as used herein includes a macromolecular matrix-forming component, such as a polypeptide (e.g. gelatin or collagen), hyaluronic acid, or polyethylene glycol, preferably gel-forming, and one or more polyhydroxy compounds. The matrix-forming component will typically be a solid at room temperature (about 25° C.). Macromolecular compounds, such as gelatin, that exhibit thermally-reversible crosslinking or gelling properties (e.g. gelling in aqueous solution at lower temperatures at reverting to flowable liquids at higher temperatures), are preferred. Preferably, the polyhydroxy compound(s) adds tackiness to the mixture. The polyhydroxy compound(s) can be glycerin, fructose or a mixture including both. Gelatin or collagen can be obtained from a collagenous material taken from any suitable source including, for instance, a bovine, porcine, fish or human source. Collagen or gelatin can also be recombinantly produced as generally known in the art. Polyhydroxy compounds are commercially available. In preferred embodiments, the tackifying polyhydroxy compound is a hygroscopic sugar such as fructose including, but not limited to D-fructose. Other polyhydroxy compounds that can be used include for instance starch, hydrolyzed starch, polysaccharides, oligosaccharides, sugars, carbohydrates, dextrin, corn syrup, and mixtures thereof. Preferred polyhydroxide compounds from these or other groups will exhibit hygroscopicity about equal to or greater than that of fructose. The polyhydroxy compound can be a liquid at room temperature (about 25° C.), such as glycerin, or may be a solid at room temperature, such as fructose. When a solid at room temperature, the fructose or other polyhydroxy compound may exhibit such a hygroscopic capacity that when exposed to air containing water vapor (humidity) at room temperature, the solid takes up water over time and becomes a syrup. Whether the polyhydroxy compound is a liquid or solid at room temperature, in certain embodiments of the invention, a matrix-forming component, such as gelatin, can serve to entrain the polyhydroxy compound and provide a matrix that when dried is relatively non-tacky and stabilized against melting to a liquid or reverting to a moistened syrup when exposed to moisture-containing air at room temperature. On the other hand, when moistened, the matrix layer becomes beneficially tacky and useful as an adhesive as described herein.

Gelatin or another polypeptide can in certain forms of the invention be included in the adhesive layer in an amount of about 1 to about 5 mg/cm$^2$, more typically about 1.9 to about 4.3 mg/cm$^2$. A polyhydroxy compound, such as fructose or glycerin or their mixture, can be included in the adhesive layer in an amount of about 1 to about 10 mg/cm$^2$, more typically about 2.7 to about 6.1 mg/cm$^2$. It will be understood that the ratio of gelatin to polyhydroxy compound(s) can be varied to achieve the desired properties e.g., tackiness, viscosity, bloom strength, melting point etc. of the resulting adhesive. As well, filling agents can be included in the adhesive to further modulate these properties. For example, polyvinyl alcohol, carboxymethycellulose, or a mixture thereof can be included in the adhesive to achieve the desired properties.

In certain embodiments, a matrix-forming macromolecule(s) (e.g. gelatin, collagen, and/or hyaluronic acid) and the tackifying polyhydroxy compound(s) will be included in a dry weight ratio of about 30:70 to about 70:30, respectively. In more preferred forms, the matrix-forming macromolecule(s) and the polyhydroxy compound(s) will be included in a dry weight ratio of about 30:70 to about 60:40, respectively, still more preferably about 30:70 to about 50:50, respectively. It will be understood, however, that other weight ratios may be used with a given combination of polypeptide and polyhydroxy compound to provide an adhesive material that, when wetted, effectively adheres an ECM or other bolster or support material to a stapler working surface and/or to patient tissue.

In certain embodiments, a particulate ECM material can be added to the adhesive, which will then be incorporated in the formed medical product. Such particulate ECM materials can be prepared by cutting, tearing, grinding or otherwise comminuting an ECM starting material. For example, a particulate ECM material having an average particle size of about 50 microns to about 500 microns may be included in the adhesive, more preferably about 100 microns to about 400 microns. The ECM particulate can be added in any suitable amount relative to the adhesive, with preferred ECM particulate to adhesive weight ratios (based on dry solids) being about 0.1:1 to about 200:1, more preferably in the range of 1:1 to about 100:1. The inclusion of such ECM particulates in the adhesive can serve to provide additional material that can function to provide bioactivity to the adhesive (e.g. itself including FGF-2 and/or other growth factors or bioactive substances as discussed herein) and/or serve as scaffolding material for tissue ingrowth.

In certain inventive embodiments, the dried adhesive is reversible such that it is non-tacky in the dried state, but becomes tacky when wetted with water or an otherwise biocompatible aqueous solution such as saline. In this manner, a medical product of the invention can be packaged and shipped in a dried state, and then wetted at the point of use (e.g. by attending medical personnel) to render the medical product tacky. In the case of staple bolster materials, the material product can then be adhered to the surgical stapler to provide a buttress for a staple or staple line. In the case of a tissue graft, the medical product can then be adhered to a tissue defect. The adhesive coating is desirably applied as a relatively thin layer, for example at a level of about 1 mg/cm$^2$ to about 100 mg/cm$^2$ on a surface of the medical material, although higher or lower levels may be used with a particular adhesive and/or bolster materials. Preferably, a level of about 4 mg/cm$^2$ to about 12 mg/cm$^2$ on a surface of a medical material is formed, although again higher or lower levels may be used in a particular circumstance.

The medical products of the present invention can be used to facilitate a variety of medical procedures. Such procedures include but are not limited to those requiring the use of a staple bolster material, such as various lung resection procedures (e.g., blebectomies, lobectomoies, bullectomies, wedge resections, and lung reduction procedures, such as those used to treat symptoms of emphysema); treatment of soft tissue injuries and defects (e.g., abdominal or thoracic wall procedures, gastrointestinal procedures), and as a tool in a variety of other surgical procedures (e.g., reproductive organ repair procedures, etc.). In this regard, the medical products of the invention may be used in conjunction with operations on both humans and animals. Likewise, when used as a bolster material, the medical products of the invention may be used with either anastomotic staplers or non-anastomotic staplers, and may be adapted, sized and shaped in a variety of ways to accommodate given stapler devices.

The medical products of the invention can be provided in sterile packaging suitable for medical products. Sterilization may be achieved, for example, by irradiation, ethylene oxide gas, or any other suitable sterilization technique, and the materials and other properties of the medical packaging will be selected accordingly.

For the purpose of promoting a further understanding of aspects of the present invention, the following specific examples are provided. It will be understood that these examples are not limiting of the present invention.

Example 1

This example demonstrates the preparation of an adhesive useful for inclusion into a medical product of the invention.

7 gm of gelatin (porcine skin type A, Sigma-Aldrich CAT #G6144) was dissolved in 20 ml of high purity water. This mixture was heated at 50° C. with constant stirring until the gelatin was completely dissolved. 50 ml of glycerin (USP grade Sigma-Aldrich CAT #G2289) was added to the mixture under constant stirring at 50° C. for 30-60 minutes. The mixture was placed in a 40° C. incubator to maintain it in a liquid state.

Example 2

This example demonstrates the preparation of a medical product of the invention using the adhesive of Example 1.

An adhesive was prepared according to Example 1 and was applied to a surface of a layer of small intestinal submucosa (SIS) to form an adhesive coating thereon. The layer of SIS including the adhesive coating was dried by lyophilization. A sheet of release paper was applied to the adhesive coating and the resulting product was packaged in a moisture impervious foil pouch and was sterilized with radiation. Just prior to use, the medical product can be removed from its packaging, and the adhesive can be exposed by peeling away the release paper. The medical product can optionally be dipped in a liquid (e.g., water or saline) to rehydrate the medical product prior to its application.

Example 3

This example demonstrates the preparation of an alternate adhesive useful in the preparation of a medical product of the invention.

7 gm of gelatin (porcine skin type A, Sigma-Aldrich CAT #G6144) and 10 gm of D-fructose (Sigma-Aldrich CAT #F9048) were dissolved in 15 ml of high purity water. This mixture was heated to 60°-90° C. with constant stirring until the gelatin was completely dissolved and a translucent amber colored solution was obtained. This mixture was placed in a 50° C. incubator to maintain it in a liquid state.

Example 4

This example demonstrates the preparation of a medical product of the invention using the adhesive of Example 3.

An adhesive was prepared according to Example 3 and was applied to a surface of a layer of small intestinal submucosa (SIS) to form an adhesive thereon. The layer of SIS including the adhesive coating was dried by lyophilization. A sheet of release paper was applied to the adhesive coating and the resulting product was packaged in a moisture impervious foil pouch and was sterilized with radiation. Just prior to use, the medical product can be removed from its packaging, and the adhesive can be exposed by peeling away the release paper. The medical product can optionally be dipped in a liquid (e.g., water or saline) to rehydrate the medical product prior to its application.

Example 5

This example demonstrates the shear strength efficacy of an adhesive as described in the present application when used in conjunction with a staple line reinforcement device. The results show that the adhesive has a shear strength at least equal to compositions currently used in staple line reinforcement applications.

To test shear strength efficacy, samples were formed from a control group and three test groups as detailed below. The control group consisted of non-aged, ethylene oxide sterilized, 4-ply, lyophilized staple line reinforcement devices currently marketed as SURGISIS® SLR™. The devices measured approximately 1.2 cm×8.8 cm in folded size when coupled to a foam applicator. To form a control group sample, the device was removed from its foam applicator and unfolded into a flat sheet measuring approximately 1.2 cm×18.4 cm. Four control group samples were formed in this manner corresponding to compression times of 5, 15, 30 and 120 seconds.

The test group consisted of E-beam sterilized (25 kGy), 4-ply, lyophilized staple line reinforcement devices currently marketed as SURGISIS® SLR™. The base material was produced as described in U.S. Provisional Patent Application Ser. No. 60/853,584, entitled "Processed ECM Materials with Enhanced Component Profiles" and filed Oct. 23, 2006. As with the control group, the finished devices were approximately 1.2 cm×8.8 cm in folded size when coupled to a foam applicator. To form the test group samples, the devices were removed from the foam applicators and unfolded into flat sheets measuring approximately 1.2 cm×18.4 cm. The first test group was composed of new, non-aged devices. The second and third test groups consisted of devices that were aged in an accelerated manner (55° C., 0-50% relative humidity) for 4 and 8 weeks, corresponding to a real-time aging of 9 and 18 months, respectively. Four test group samples were formed from each test group for a total of 12 test group samples.

Each test group sample also included an adhesive of the present application. An adhesive was prepared for application to the test group samples in a manner that would theoretically limit the tack of the adhesive. To prepare this adhesive, 21.5 g of porcine Type-A Gelatin and 29 g of fructose were mixed in high purity water with constant stirring and heating (70+10° C.) for approximately 20-25 minutes. While still in a molten state, the adhesive was coated on a surface of each test group sample and dried under vacuum.

Once the control group samples and test group samples were prepared, a test apparatus comprised of two flat, hinged sheets of 0.25" Delrin was formed. A flat sheet of stainless steel, with a pre-specified surface finish and etched markings along the edge at 1.0 cm intervals, was attached to the top piece of Delrin. The test apparatus was cleaned with 70% isopropyl alcohol (IPA) and lint-free wipes and affixed to the edge of a lab bench top. A line of Kendall Dover sterile lubricating jelly (for the control group samples) or high purity water (HPW, for the test group samples), equivalent to the length of the sample (+3 mm), was applied to the longitudinal axis of the stainless steel plate. The amount of hydrogel or HPW applied, other than the length of application, was not controlled.

A total of 16 samples were prepared as described above. One sample at a time was gently placed over the line of hydrogel (control group samples) or HPW (test group samples), while allowing approximately 5 mm (+2 mm) to hang over the edge of the stainless steel plate for attachment of a test weight. A test weight of approximately 71.96 g was affixed to this end of the device in order to provide a tension to the sample adhered to the apparatus. Since this test was designed only to compare groups, the test weight was selected via preliminary testing in order to maximize the potential to differentiate between the two groups (too much weight and all samples would fail, while too little weight and all samples would pass).

A first timer was pre-set to count down from a designated compression time of either 5, 15, 30 or 120 seconds. The compression time simulates the period of time an operator applies compression force to the SLR device after insertion between the jaws of the stapler to enable adhesion. A second timer was set to count down from 5 seconds to measure the success or failure of a particular sample.

A compression block weighing approximately 11.6 pounds was placed on the sample adhered to the test apparatus, which was within the range of closing force of commercially available staplers. The first timer was started at the same time the compression block was placed onto the sample. Once the first timer read zero, the compression block was removed from the sample and the stainless steel plate was quickly rotated 90° so that it was perpendicular to the ground. The test weight assembly was supported by hand during the 90° rotation. Support of the test weight was discontinued immediately after the stainless steel plate was rotated 90°, and the second timer was immediately started thereafter. The sample was observed for movement relative to the etched markings on the steel plate. If the device traveled downward by a distance of 1.0 cm or greater in 5 seconds the test was designated as a failure. If the device did not move, or traveled downward by a distance of less than 1.0 cm in 5 seconds, the test was designated as a success. This process was repeated for all 4 control group samples with hydrogel being applied to the stainless steel plate and for all 12 test group samples with HPW being applied to the stainless steel plate. The stainless steel plate and compression block were cleaned using 70% IPA and lint-free wipes between sample testing.

The results were calculated as the ratio of successes to overall number of tests. Table 1 displays a summary of the success rates of the various shear strength tests:

| Compression Time (sec) | Control SLR w/ hydrogel (non-aged) | SLR w/ adhesive (non-aged) | SLR w/ adhesive (9 month accelerated aging) | SLR w/ adhesive (18 month accelerated aging) |
| --- | --- | --- | --- | --- |
| 5 | 30% | 100% | 100% | 73% |
| 15 | 70% | 100% | 100% | 100% |
| 30 | 100% | 100% | N/C* | N/C* |
| 120 | 100% | 100% | N/C* | N/C* |

*N/C - Testing was not conducted because 100% success was achieved at a lower time point. Extended compression times only increase the tack of the adhesive, thereby making further testing unnecessary.

Statistical analysis was employed in addition to direct comparison of success rates. Table 2 summarizes the statistical output as a p-value of the shear strength testing based on Fisher's exact tests between groups. The Fisher's exact test was deemed most appropriate for statistical analysis due to the binomial proportions and the small number of failures.

| Compression Time (sec) | Control vs. SLR w/ adhesive (non-aged) | Control vs. SLR w. adhesive (9 month accelerated aging) | Control vs. SLR w/ adhesive (18 month accelerated aging) |
| --- | --- | --- | --- |
| 5 | p = 0.003 | p = 0.003 | p = 0.083 |
| 15 | p = 0.211 | p = 0.528 | p = 0.211 |
| 30 | p = 1 | N/C* | N/C* |
| 120 | p = 1 | N/C* | N/C* |

*N/C - Testing was not conducted because 100% success was achieved at a lower time point. Extended compression times only increase the tack of the adhesive, thereby making further testing unnecessary.

Based on the success rates defined above, the SLR device with an adhesive of the present application had an adhesive strength at least equal to or greater than the control at zero (non-aged), 9 and 18 months. The SLR device including an adhesive of the present application had a statistically significant greater adhesive strength than the control at zero (non-aged) and 9 months with a 5 second compression time. Additional analysis using Fisher's exact test showed that there was no statistically significant difference between the adhesive strength of non-aged SLR devices with an adhesive of the present application and SLR devices with an adhesive of the present application that had been aged for 18 months.

These results evidence that an SLR device with an adhesive of the present application can be used in staple line reinforcement applications.

Example 6

Preparation of an Alternative Gelatin Material

Gelatin can be derived from porcine small intestinal submucosal tissue (SIS) as follows. SIS material is heated to 60° C. to 95° C. in a bath of high purity water (1:10 to 1:20 ratio, weight SIS:volume high purity water) for at least 2 hours. The high purity water solution is separated from the spent SIS material and is collected for drying. The high purity water solution is dried and the resultant dry gelatin-containing material is used instead of the commercially-obtained gelatin in the preparation of adhesive compositions as described in Examples 1-5 above.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. In addition, all publications cited herein are indicative of the abilities of those of ordinary skill in the art and are hereby incorporated by reference in their entirety as if individually incorporated by reference and fully set forth.

What is claimed is:

1. A medical product, comprising:
   a medical graft material; and
   a dried, reversible adhesive coating on at least a portion of a surface of said material, wherein said adhesive coating comprises a mixture of gelatin and fructose, wherein said fructose is present in the adhesive coating in an amount greater than that of said gelatin by dry weight ratio and in an amount of 1 to 10 mg/cm$^2$, wherein said adhesive coating has a dry weight ratio of gelatin to fructose of 30:70 to 50:50, wherein said adhesive coating comprises a layer present at a level of 2 mg/cm$^2$ to 100 mg/cm$^2$; and wherein said reversible adhesive coating is suitable when wetted to attach said medical graft material to a surgical device while allowing for the release of the medical graft material from the surgical device upon implantation.

2. The medical product of claim 1, wherein said reversible adhesive coating is non-tacky when dried, and wherein said reversible adhesive coating becomes tacky when moistened.

3. The medical product of claim 1, wherein said medical graft material is comprised of a biological material.

4. The medical product of claim 3, wherein said medical graft material is remodelable.

5. The medical product of claim 4, wherein said medical graft material comprises an extracellular matrix (ECM) material.

6. The medical product of claim 5, wherein said ECM comprises submucosa.

7. The medical product of claim 6, wherein said submucosa is intestinal, urinary bladder or stomach submucosa.

8. The medical product of claim 7, wherein said submucosa is small intestinal submucosa (SIS).

9. The medical product of claim 1, wherein said medical product is useful as a bolster material.

10. The medical product of claim 9, wherein said bolster material is configured for application to an arm of a surgical fastening device.

11. The medical product of claim 1, wherein said medical product is useful as a hernia repair graft.

12. The medical product of claim 1, wherein said adhesive is dried to form a porous open-cell foam.

13. The medical product of claim 1, wherein said adhesive further comprises a bioactive component and/or pharmaceutical agent.

14. The medical product of claim 1, wherein said adhesive is coated onto a substantial portion of the medical material.

15. The medical product of claim 1, wherein said adhesive is air dried.

16. The medical product of claim 1, wherein said adhesive is vacuum dried.

17. A medical product for use with a surgical device, said medical product comprising:
    a layer of dried, collagenous extracellular matrix material; and
    a dried, reversible adhesive coating on at least a portion of a surface of said layer, wherein said adhesive comprises a mixture of gelatin and fructose, wherein said mixture contains a greater amount of fructose than gelatin on a dry weight basis, wherein said adhesive coating has a dry weight ratio of gelatin to fructose of 30:70 to 50:50, and wherein said reversible adhesive coating is suitable when wetted to attach said medical graft material to the surgical device while allowing for the release of the medical graft material from the surgical device upon implantation.

18. The medical product of claim 17, wherein said layer and said coating are lyophilized.

19. The medical product of claim 17, wherein said layer comprises submucosa of a warm-blooded vertebrate.

20. The medical product of claim 19, wherein said layer comprises small intestinal submucosa.

21. The medical product of claim 17, wherein said adhesive is air dried.

22. The medical product of claim 17, wherein said adhesive is vacuum dried.

23. A bolster material, comprising:
    bolster material configured for application to an arm of a surgical fastening device; and
    a dried, reversible adhesive coating on at least a portion of a surface of said bolster material, wherein said adhesive comprises a mixture of gelatin and fructose, and wherein said gelatin is present in the adhesive in an amount of 1 to 5 mg/cm$^2$, wherein said fructose is present in the adhesive in an amount greater than that of said gelatin by dry weight, wherein said adhesive comprises at least 30% but less than 50% gelatin on a dry weight basis, and wherein said reversible adhesive coating is suitable when wetted to attach said bolster material to the arm of the surgical fastening device while allowing for the release of the bolster material from the arm of the surgical fastening device upon implantation.

24. The bolster material of claim 23, wherein said adhesive coating has a dry weight ratio of gelatin to fructose of 30:70 to 50:50.

* * * * *